US00PP31877P2

(12) United States Plant Patent
Kleinwee

(10) Patent No.: US PP31,877 P2
(45) Date of Patent: Jun. 16, 2020

(54) *CHRYSANTHEMUM* PLANT NAMED 'CIFZ0071'

(50) Latin Name: ***Chrysanthemum* x *morifolium***
Varietal Denomination: CIFZ0071

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,899

(22) Filed: Jan. 31, 2019

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ..... A01H 6/1424; A01H 5/02
See application file for complete search history.

*Primary Examiner* — Keith O. Robinson
(74) *Attorney, Agent, or Firm* — Dale Skalla

(57) ABSTRACT

A new garden type *Chrysanthemum* plant named 'CIFZ0071' particularly distinguished by a compact size plant with round mound plant habit, a medium (1.75 inch) size, red flower color and a natural season response in early-mid October.

1 Drawing Sheet

Figure 1:
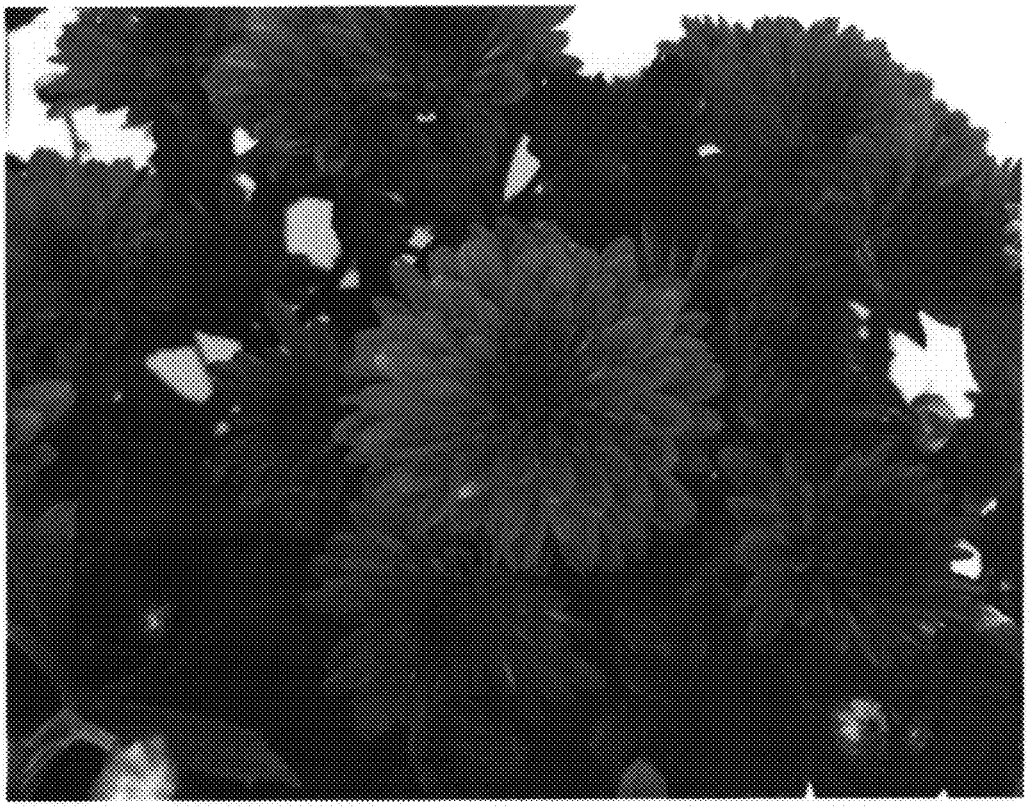

Latin name of the genus and species of the plant claimed: *Chrysanthemum* x *morifolium*.

Varietal denomination: 'CIFZ0071'.

BACKGROUND OF THE NEW PLANT

The present invention comprises a new *Chrysanthemum*, botanically known as *Chrysanthemum* x *morifolium*, and hereinafter referred to by the variety name 'CIFZ0071'.

'CIFZ0071' is a product of a planned breeding program. The new cultivar has a compact size plant with round mound plant habit, a medium (1.75 inch) size, red flower color and a natural season response in early-mid October.

'CIFZ0071' originated from a cross made in March 2014 in Enkhuizen, The Netherlands. Seeds were sown in June 2014 in Enkhuizen, The Netherlands and 'CIFZ0071' was selected from the resulting population on Nov. 4, 2014 in Enkhuizen, The Netherlands.

The female parent was the seedling '09-M303', not patented.

When compared to the female parent, 'CIFZ0071' has/is:

a similar flower size and color but less disc florets than the female parent.
a half week faster with blackcloth and one week slower for natural season response than the female parent.
a similar plant habit but smaller overall plant size than the female parent.

The male parent was the seedling '10-M003', not patented.

When compared to the male parent, 'CIFZ0071' has/is:

a similar flower size and type but flower color is red not lavender two-tone like the male parent.
a half week faster blackcloth response and a one week faster natural season response than the male parent.
a similar plant habit but smaller overall plant size than the male parent.

The first act of asexual reproduction of 'CIFZ0071' was accomplished when vegetative stem cuttings were propagated from the initial selection in January 2015 in Enkhuizen, The Netherlands.

BRIEF SUMMARY OF INVENTION

Horticultural examination of plants grown from cuttings of the plant initiated in January 2015 and continuing thereafter, has demonstrated that the combination of characteristics as herein disclosed for 'CIFZ0071' are firmly fixed and are retained through successive generations of asexual reproduction.

'CIFZ0071' has not been observed under all possible environmental conditions. The phenotype may vary significantly with variations in environment such as temperature, light intensity and day length.

A Plant Breeder's Right for this cultivar has not yet been applied for. 'CIFZ0071' has not been made publicly available prior to the effective filing date of this application, notwithstanding any disclosure that may have been made less than one year prior to the effective filing date of this application by the inventor or another who obtained 'CIFZ0071' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0071' with colors being as true as possible with an illustration of this type.

Figure 2:
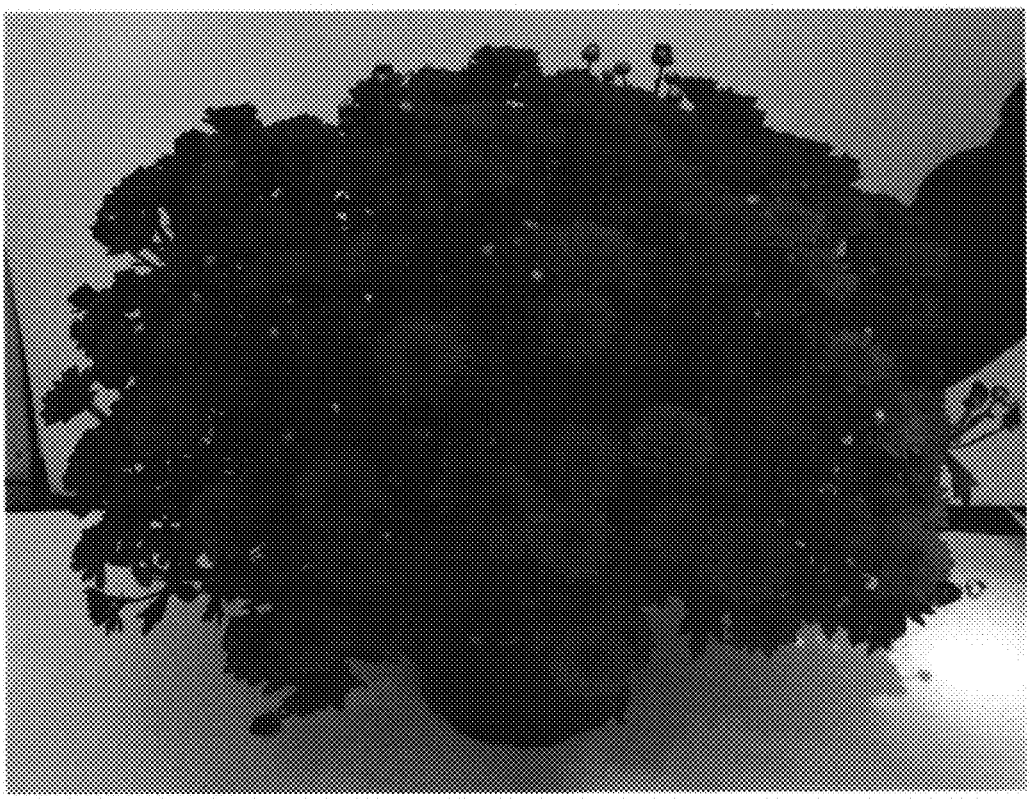

The photographic drawing shows in FIG. 1 a close view of flowers of the new variety and in FIG. 2 a flowering plant from an outdoor trial.

The aforementioned photographs: FIG. 1, as well as FIG. 2, were taken in August 2018 both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2018 on the plants from the aforementioned trial.

Color references are made to The Royal Horticultural Society Colour Chart (R.H.S.) 2015.

TABLE 1

DIFFERENCES BETWEEN THE NEW VARIETY 'CIEZ0071' AND TWO MOST SIMILAR VARIETIES:

| | 'CIFZ0071' | 'Emelda Red' (Unpatented) |
|---|---|---|
| Flowering response (blackcloth): | Half a week faster blackcloth response | Half a week slower blackcloth response |
| flowering response (natural): | Similar natural season response | Similar natural season response |
| Flower color: | Similar flower color | Similar flower colour color |
| Flower size: | Large | Smaller |
| Doubleness flower: | Double | Semi double |
| Plant habit or size: | Similar plant size and plant habit | Similar plant size and plant habit |

| | 'CIFZ0071' | 'Thera Red' (U.S. Plant Pat. No. 28,182) |
|---|---|---|
| Flowering response (blackcloth): | As much as two weeks faster to flower in blackcloth | As much as two weeks slower to flower in blackcloth |
| Flowering response (natural): | Similar natural season response | Similar natural season response |
| Flower color: | Darker initial red flower color | Lighter initial red flower color |
| Flower size: | Bit smaller flower size | Bit bigger flower size |
| Plant habit or size: | Smaller overall plant size because of less plant height | Bigger overall plant size because of more plant height |

Plant:

*Form, growth and habit.*—Herbaceous garden-type, stems upright and outwardly spreading, freely branching, strong and moderately vigorous growth habit.

*Plant height (above soil).*—5-15 cm.

*Plant height (inflorescence included).*—16-23 cm.

*Plant width.*—39-42 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS 137A.

*Mature leaf, color lower surface.*—RHS NN137C.

*Length.*—5.5-5.6 cm.

*Width.*—4.7-4.3 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS N138A.

*Pattern of veining.*—Palmate.

*Petiole color.*—RHS 137A.

*Petiole length.*—1.1-1.2 cm.

*Diameter.*—0.2-0.3 cm.

*Texture.*—Covered with bifid hairs.

Stem:

*Quantity of main branches per plant.*—6 to 8.

*Color of stem.*—RHS 138A.

*Length of stem.*—8.2-9.1 cm.

*Diameter.*—0.5 cm.

*Length of internodes.*—1.5-1.8 cm.

*Texture.*—Bifid hairs.

*Color of peduncle.*—RHS 138A.

*Length of peduncle.*—5.5-6.1 cm.

*Peduncle diameter.*—0.3 cm.

*Texture.*—Bifid hairs.

Inflorescence:

*Type.*—Compositae, solitary, decorative type inflorescences borne terminally above foliage, ligulate ray florets florets arranged on a capitulum.

*Quantity of short days to flowering (response time).*—Approximately 6.5 weeks.

*Natural season flowering.*—Early to mid-October.

*Quantity of inflorescences per plant.*—170-180.

*Lastingness of individual blooms on the plant.*—About 4.5 weeks from first color.

*Fragrance.*—Slightly spicy.

Bud (when showing color):

*Color.*—RHS 46A.

*Length.*—1.3 cm.

*Width.*—1.2 cm.

*Shape.*—Oblate.

Immature inflorescence:

*Diameter.*—3.6 cm.

*Color of ray florets, upper surface.*—RHS 46A, overlain with RHS 15A.

*Color of ray florets, lower surface.*—RHS 7A with some spots RHS 46A.

Mature inflorescence:

*Diameter.*—3.9 cm.

*Depth.*—1.4 cm.

*Total diameter of disc.*—No disc present.

*Receptacle color.*—RHS 46A.

*Receptacle height.*—0.3 cm.

*Receptacle diameter.*—0.5 cm.

Ray florets:

*Average quantity of florets.*—Between 180 and 190 in several whorls.

*Color of florets, upper surface (abaxial).*—RHS 46A, overlain with RHS 15A.

*Color inner surface (adaxial).*—RHS 46A overlain with RHS 7A.

*Length.*—1.9 cm.

*Width/diameter.*—0.5 cm.

*Shape.*—Elliptical.

*Apex shape.*—Most obtuse and dentate.

*Base shape*.—Tube.
*Margin*.—Entire, small incisions may occur at the tip.
*Texture, upper surface*.—Papillate.
*Lower surface*.—Papillate.

Disc florets: None.

Phyllaries:
*Quantity*.—30-40.
*Color, upper surface*.—RHS 143C.
*Color, lower surface*.—RHS 143A.
*Length*.—0.8 cm.
*Width*.—0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.5 cm.
*Style color*.—RHS 150A.
*Style length*.—0.3 cm.
*Stigma color*.—RHS 7B.
*Stigma shape*.—Bi-parted.
*Ovary color*.—RHS 145C.
*Ovary length*.—0.2 cm.
*Ovary width*.—0.1 cm.

Androecium:
*Stamens*.—None (are normally present in disk florets, these are not developed).
*Fertility/seed set*.—Not determined to date.
*Disease/pest resistance*.—Has not been determined to date.

What is claimed is:

1. A new and distinct variety of *Chrysanthemum* plant named 'CIFZ0071' substantially as illustrated and described herein.

* * * * *